(12) United States Patent
Wang et al.

(10) Patent No.: US 11,072,637 B2
(45) Date of Patent: Jul. 27, 2021

(54) WALNUT OLIGOPEPTIDE POWDER, PREPARATION METHOD AND APPLICATION THEREOF

(71) Applicant: Sinphar Tian-Li (Hangzhou) Pharmacy Company Limited, Zhejiang (CN)

(72) Inventors: Zhaori Wang, Zhejiang (CN); Mingchuan Liu, Zhejiang (CN); Shengjie Yang, Zhejiang (CN); Da Hong, Zhejiang (CN); Jinping Yang, Zhejiang (CN)

(73) Assignee: SINPHAR TIAN-LI (HANGZHOU) PHARMACY COMPANY LIMITED, Zhejiang (CN)

( * ) Notice: Subject to any disclaimer, the term of this patent is extended or adjusted under 35 U.S.C. 154(b) by 0 days.

(21) Appl. No.: 16/071,583

(22) PCT Filed: Jan. 18, 2017

(86) PCT No.: PCT/CN2017/000121
§ 371 (c)(1),
(2) Date: Jul. 20, 2018

(87) PCT Pub. No.: WO2017/124921
PCT Pub. Date: Jul. 27, 2017

(65) Prior Publication Data
US 2019/0276504 A1    Sep. 12, 2019

(30) Foreign Application Priority Data
Jan. 22, 2016  (CN) .......................... 201610043952.0

(51) Int. Cl.
| | | |
|---|---|---|
| *C07K 14/415* | (2006.01) | |
| *A23L 33/185* | (2016.01) | |
| *A23J 3/34* | (2006.01) | |
| *A61K 38/01* | (2006.01) | |
| *C07K 1/34* | (2006.01) | |
| *C12P 21/06* | (2006.01) | |
| *C07K 2/00* | (2006.01) | |
| *A61K 38/02* | (2006.01) | |
| *C07K 1/14* | (2006.01) | |
| *A61K 8/64* | (2006.01) | |
| *A61P 25/28* | (2006.01) | |
| *A23J 1/14* | (2006.01) | |
| *B01D 61/14* | (2006.01) | |

(52) U.S. Cl.
CPC ............ *C07K 14/415* (2013.01); *A23J 1/148* (2013.01); *A23J 3/346* (2013.01); *A23L 33/185* (2016.08); *A61K 8/64* (2013.01); *A61K 38/011* (2013.01); *A61K 38/02* (2013.01); *A61P 25/28* (2018.01); *B01D 61/142* (2013.01); *B01D 61/145* (2013.01); *B01D 61/147* (2013.01); *C07K 1/14* (2013.01); *C07K 1/34* (2013.01); *C07K 2/00* (2013.01); *C12P 21/06* (2013.01); *A23V 2002/00* (2013.01)

(58) Field of Classification Search
None
See application file for complete search history.

(56) References Cited

FOREIGN PATENT DOCUMENTS

| | | | |
|---|---|---|---|
| CN | 101228918 A | 7/2008 | |
| CN | 101280327 A | 10/2008 | |
| CN | 102406050 A | 4/2012 | |
| CN | 103109971 A | 5/2013 | |
| CN | 103125735 A | 6/2013 | |
| CN | 103484518 A | 1/2014 | |
| CN | 103497985 A | 1/2014 | |
| CN | 104031968 A | 9/2014 | |
| CN | 103103244 B | 12/2014 | |
| CN | 104293870 A | 1/2015 | |
| CN | 105002247 A | 10/2015 | |
| CN | 105567774 A | 5/2016 | |
| CN | 105567774 A * | 5/2016 | ............. A61K 38/02 |
| CN | 105936927 A * | 9/2016 | |
| JP | 2007513612 A | 5/2007 | |
| WO | 2004013170 A1 | 2/2004 | |
| WO | 2005120244 A1 | 12/2005 | |

OTHER PUBLICATIONS

Liu et al. "A simple and convenient method for the preparation of antioxidant peptides from walnut (*Juglans regia* L.) protein hydrolysates" Chemistry Central Journal 10:39 (Year: 2016).*
Liu, Gao Jian-Ping, et al., "Extraction of Soybean Protein Isolate Using Multi-stage Countercurrent Solid-Liquid Extraction Method", The Chinese Journal of Process Engineering, vol. 11, No. 2, Apr. 15, 2011, pp. 312-317 (w/ English abstract).

* cited by examiner

*Primary Examiner* — Sudhakar Katakam
*Assistant Examiner* — Zachary J Miknis (57) ABSTRACT

The present invention provides a walnut oligopeptide powder, a preparation method and application thereof. The oligopeptide powder has a peptide content of 80 wt % or higher, in which 95% or more of the peptides have a molecular weight of less than 1,500 Da. The method includes extracting walnut proteins using a highly efficient countercurrent extraction process, and subjecting the extract to filtration, enzymolysis, purification with a microfiltration membrane and an ultrafiltration membrane, concentrating, and spray drying to obtain the oligopeptide powder. The oligopeptide powder has an anti-oxidant activity and provides a protective effect for a neuron, and thus can ameliorate or treat memory deterioration and relieve fatigue.

1 Claim, 6 Drawing Sheets

WALNUT OLIGOPEPTIDE POWDER, PREPARATION METHOD AND APPLICATION THEREOF

CROSS-REFERENCE TO RELATED APPLICATION

This application is a National Stage Entry under 35 U.S.C. § 371 of International application No. PCT/CN2017/000121, filed Jan. 18, 2017 which claims the benefits of priority of CN application No. 201610043952.0 filed on Jan. 22, 2016, the content of which are incorporated herein by reference.

BACKGROUND

Field of Invention

The invention relates to a walnut oligopeptide product with high purity and low molecular weight. The polypeptide content is more than 80 wt %, and the molecular weight of less than 1500 Dalton is more than 95%. The invention further relates to a preparation method of a walnut protein, catalytic enzymolysis thereof, and forming oligopeptide powder. The peptide powder can be used as medicines, foods, health-supplement or cosmetics. This application claims priority to Chinese Application CN201610043952.0, which is herein incorporated by reference.

Description of Related Art

Walnut is also known as *Juglans regia*, belongs to one of the four big nuts and has very high nutritional medicinal value. In ancient Chinese medicine books, an explicit record is provided. "Compendium of Materia Medica" written by Li, Shizhen has recorded that the walnut has the functions of tonifying qi and nourishing blood, moistening dryness and reducing phlegm, prolonging the life and clearing heat-dampness in sanjiao, warming the lung and moistening the intestines, treating the lung and moistening the intestines, treating asthenia cold and asthmatic cough, treating swelling and pain of lumbar and foot, treating confidants colic, treating dysentery, and easing swell poison. "Kai Bao Ben Cao" written by Song, Liuhan has described that *Juglans regia* (namely walnuts) is sweet, flat and non-toxic. It has the effects of promoting the human body to strengthen the spleen, moistening the muscles and blackening hair, taking the pulp and burning the black, and not breaking the smoke and the rosin. "Shi Liao Ben Cao" written by Meng Shen in the Tang Dynasty, and the walnut can be used for dredging meridians and blacking hair, the meat and bone is fine and smooth by regular using. "Shi Jing" written by Cui Yuxi has recorded that it can facilitate urination and remove five hemorrhoids by eating more walnuts. The functions of tonifying the kidney, moistening the door, securing essence and moistening the intestines, clearing away heat and toxic materials, stopping cold and purging deficiency diarrhea and the like were described in the book of "Yi Lin Cuan Yao".

Walnut contains rich nutrients such as protein, fat and the like, is balanced in content, and belongs to a relatively ideal high protein, the high-fat food. It is reported that the walnut kernels contain up to 52%-70% of fat, which are mostly unsaturated fatty acids, and further contains about 24% of protein and 12-16% of carbohydrate, 1.5%-2% of cellulose and 1.7%-2% of mineral substances. The walnut is rich in amino acid essential to human body, is relatively reasonable in amino acid proportion. The content of glutamic acid, aspartic acid, and arginine that have important functions of the human body physiological function are relatively high. And glutamic acid is an important functional substance affecting the intelligence and memory development of the human body, especially the adolescents.

To obtain better oligopeptide powder compared with the original protein of the walnut in the aspect of nutrition, function and biological activity, a plurality of preparation methods have been tried. The method disclosed in CN101228918A comprises the following steps: crushing walnut residue, and extracting the walnut protein by an ultrasonic method, the walnut protein is subjected to vacuum drying, then the walnut protein is subjected to enzymolysis by using protease, and the walnut protein is centrifuged, carrying out dialysis on the supernatant by using a dialysis bag, concentrating the dialysate and carrying out vacuum drying to obtain the peptide powder with the content of 60%-80%. The method is complex in operation, the content of the peptide is low, and the distribution of the molecular weight of the peptide is not clear, meanwhile, the ultrasonic extraction protein is used, the dialysis bag is refined, and large-scale preparation cannot be carried out. The method disclosed in CN102406050 A comprises the following steps: extracting protein by using an alkaline extraction acid pre-cipitation method, and carrying out freeze drying to obtain the walnut protein powder, the protein powder is subjected to enzymolysis, and the protein powder is subjected to high-pressure treatment at 300 MPa for 10 minutes, and freeze-drying to obtain the walnut peptide powder. The preparation method requires ultrahigh pressure equipment and a freeze drier, is high in cost and is not suitable for large-scale production; the molecular weight distribution of the walnut peptide powder prepared by the method is not clear, and the content of the peptide in the product is not clear. The method disclosed in CN103103244 B comprises the following steps: extracting protein by using a method for carrying out acid precipitation by using an alkali extraction acid precipitation method, and carrying out ultrasonic treatment on the protein by using microwaves. The method is still not suitable for large-scale production, and the content of the peptide in the enzymatic hydrolysate is not measured. The Patent CN104293870 A comprises the following steps: firstly, removing grease by using a $CO_2$ supercritical extraction instrument to obtain walnut residue, carrying out alkali extraction and acid precipitation and then spraying to obtain the walnut protein powder, then making the protein powder into turbid liquid, boiling to destroy the structure of the protein, and using alkaline protease, papain, neutral protease and bromelain in a segmented four-step enzymolysis walnut protein solution, 5000 Dalton or 8000 Dalton ultrafiltration membrane is used for refining, and then ion exchange resin desalination is used, and finally spraying and drying to obtain the walnut peptide powder. The patent relates to the application of the supercritical extraction instrument when grease is removed, the cost is increased, and the method is not easy to produce; the four enzymes of the four-step enzymolysis are involved, the steps are tedious, and the cost is high; after the enzymolysis is completed, the micro-filtration membrane is not subjected to impurity removal, the ultra-filtration membrane is directly subjected to an ultrafiltration membrane, so that the ultrafiltration membrane is easy to block, and the ultrafiltration time is prolonged, the yield of the polypeptide is reduced, and meanwhile the service life of the ultrafiltration membrane is shortened. The content of the peptide in the polypeptide product and the molecular weight distribution of the peptide are not involved in the method.

Therefore, the preparation conditions of the walnut polypeptide are rigorous, and the process steps are tedious, large-scale production is difficult to realize. And the simple, low cost and large-scale production method of the walnut polypeptide with relatively high activity and high content has become one of research hotspots.

SUMMARY

The invention aims to provide a walnut oligopeptide powder with high purity and low molecular weight.

Another object of the invention is to provide a preparation method of high purity and low-molecular-weight walnut oligopeptide powder.

The invention aims to provide the walnut oligopeptide powder which is used for preparing medicines, foods, health-supplement or cosmetics for treating or preventing the symptoms caused by excessive free radicals.

The invention aims to provide the walnut oligopeptide powder which is used for preparing medicines, foods, health-supplement or cosmetics for improving or treating memory recession.

Another object of the invention is to provide the walnut oligopeptide powder which is used for preparing medicines, foods, health-supplement or cosmetics for treating or preventing Parkinson's disease, Alzheimer's disease, or relieving brain or exercise fatigue.

The invention aims to provide the walnut oligopeptide powder which is used for preparing medicines, foods, health-supplement or cosmetics for enhancing immunity.

Another object of the invention is to provide drugs, foods, health-supplement or cosmetics composition containing the walnut oligopeptide powder in the invention.

The objects of the invention are achieved by the following technical solutions.

A walnut oligopeptide powder is characterized in that: the content of the oligopeptide is more than 80 wt % applying detection Methods in GB/T 22492-2008, Appendix A and Appendix B. The molecular weight of more than 95% of the walnut oligopeptide is less than 1500 Dalton, and the molecular weight distribution of the walnut peptide is as follows:

| Molecular Weight Dalton Distribution | |
| --- | --- |
| Range of Molecular Weight | Peak Area Percentage %, λ 220 nm |
| >1500 | <1 |
| 1500~1300 | 7~8 |
| 1300~500 | 20~25 |
| 500~200 | 50~55 |
| <200 | <20 |

Range of Number-Average Molar Mass: 170~3000
Range of Weight-Average Molar Mass: 180~4000.

Preferably, the peptide content is 81 wt % or more, and more than 97% of the oligopeptide has a molecular weight of less than 1500 Dalton. More Preferably, the peptide content is 81.3 wt % or more, and more than 96% of the oligopeptide has a molecular weight of less than 1500 Dalton. Preferably, the content of the peptide is more than 85 wt %, and more than 97% of the oligopeptide has a molecular weight of less than 1500 Dalton. Most preferably, the content of the peptide is more than 85 wt %, and more than 96% of the oligopeptide has a molecular weight of less than 1500 Dalton.

The walnut oligopeptide powder is prepared by the following method:

(1) Preprocessing of walnut residue: shelling walnuts, carrying out cold pressing and degreasing to obtain degreased walnut residue.

(2) Protein extracting by a high-efficiency countercurrent extraction method: recording a certain amount of degreased walnut residue as A and mixing A with water at the weight ratio of 1:5-1:15, adjusting the pH value to 9-11, and extracting for 1-2 hours at the room temperature; after the extraction is completed, filtrating, carrying out a secondary extraction on the filtered residue, pouring an equal amount of walnut residue into the filtrate and recording the mixture as B, adjusting the pH value to 9-11, and extracting for 1-2 hours at room temperature; after the first extraction of B is completed, setting aside the filtrate, and carrying out a secondary extraction on the filtered residue; after the secondary extraction of A is completed, abandoning the filtered residues, and pouring an equal amount of walnut residue into the filtrate and recording the mixture as C, adjusting the pH value to 9-11, and extracting for 1-2 hours at the room temperature; after the secondary extraction of B is completed, abandoning the filtered residues, pouring the filtrate into the filtered residue from the first extraction of C and extracting for 1-2 hours, and setting aside the filtrate from the first extraction of C; carrying out a secondary extraction of C, abandoning the filter residue and setting aside the filtrate; finally, merging all the filtrates, adjusting the pH value to be 3-5, and standing for 0.5-2 hours, removing the supernatant, and finally adding the water into the precipitate, in which the volume ratio of the water to the precipitate is 1:10 to 1:20, and uniformly stirring to obtain walnut protein solution.

(3) Protein enzymolysis: heating the walnut protein solution to 40-55° C., adjusting the pH value to neutral, adding enzyme in the weight of 0.5-2% based on the weight of the walnut residue, stirring during enzymatic hydrolysis for 3-6 hours, and then boiling to inactivate for 30 minutes, centrifuging, in which the supernatant is an enzymatic proteolysate liquid.

(4) Separating and purifying: filtrating the enzymatic proteolysate liquid with a micro-filtration membrane with the pore diameter of 0.1-0.5 microns, filtrating the permeate with a 2000-20000 Dalton ultrafiltration membrane, and then concentrating the retentate at the temperature of 50-80° C. until the solid content is 3-5 wt %, carrying out spray drying, in which the inlet temperature is 140-160° C., and the outlet temperature is 55-65° C., obtaining the high-purity, low-molecular-weight walnut oligopeptide powder, in which the yield is 20-30 wt %.

(5) Measurement of the Peptide content and the molecular weight distribution: by applying Methods GB/T 22492-2008, Appendix A and Appendix B, the content of the oligopeptide is more than 80 wt %, in which 95% of the walnut peptide has a molecular weight of less than 1500 Dalton.

The biological enzyme is selected from food-grade neutral protease (enzyme activity is greater than or equal to 300,000 u/g), papain (enzyme activity is greater than or equal to 400,000 u/g), bromelain (enzyme activity is greater than or equal to 300,000 u/g), and alkaline protease (enzyme activity is greater than or equal to 200,000 u/g), pepsin (enzyme activity is greater than or equal to 500,000 u/g), pancreatin (enzyme activity is greater than or equal to 3000 u/g) or a mixture thereof. The neutral protease or a complex enzyme is preferred, in which a mass ratio of the neutral protease to the papain in the complex enzyme is 1:1, the activity of the neutral protease is 300,000 u/g, and the activity of the papain is 500,000 u/g.

The invention provides a composition containing the walnut oligopeptide powder and the acceptable additive in medicines, foods, health-supplement or cosmetics.

According to the prior art, the composition can be prepared into any dosage form, for example, tablet, film-coated tablet, sugarcoating tablet, enteric-coated, dispersible tablet, capsules, granule, oral solution, oral suspension, or a cosmetic dosage form, such as liquid, emulsion, cream, powder, block, and the like.

The walnut oligopeptide powder of the invention may be used for preparing medicaments, foods, health-supplement or cosmetics for treating or preventing symptoms caused by excessive free radicals; and may be used for preparing medicaments, foods, health-supplement or cosmetics for improving or treating memory recession; and may be used for preparing medicaments, foods, health-supplement or cosmetics treating or preventing Parkinson's disease and Alzheimer's disease, and relieving the brain or exercise fatigue; and may be used for preparing medicaments, foods, health-supplement or cosmetics for enhancing immunity.

Compared with the prior art, the invention has the following advantages:

(1) According to the method, the walnut residue is prepared by cold pressing and degreasing of walnuts. Relevant experiments were carried out by the inventor. Compared with a hot pressing method, after cold pressing, the protein extraction rate is higher by 5 wt %, and the content is higher by 20 wt %.

(2) The method disclosed by the invention is used for extracting the walnut protein by using a high-efficiency countercurrent method. Compared with a common alkali extraction acid precipitation method, the extraction rate of the protein is increased by more than 10%, the water consumption is reduced, and the production cost is reduced.

(3) Enzymolysis is carried out only by using a protein complex solution, and protein is not dried, so that the loss of protein drying is reduced, and the preparation process is simplified.

(4) The biological enzyme disclosed by the invention can be ensured in terms of content, molecular weight, yield and activity, and the enzymolysis process is stable. The two enzymes are edible enzymes, the source is wide, and the cost is low. During enzymolysis, the adding amount is only 0.5-2% of the mass of the walnut residue.

(5) Filtrating by using a microfiltration membrane to preliminarily remove insoluble substances in the enzymatic hydrolysate, and removing the large-molecular-weight protein by using a 2000-20000 Dalton ultrafiltration membrane.

(6) No freeze-drying or vacuum drying method is used for preparing the product, the drying time is saved, and the product quality is uniform.

(7) In the present invention, the molecular weight distribution of the polypeptide is determined according to Method GB/T 22492-2008, Appendix A, and the content of acid-soluble protein and free amino acid are determined according to Appendix B, and finally, the difference value is the peptide content. The determination method for the molecular weight and the peptide content is highly recognized.

| Molecular Weight Dalton Distribution | |
|---|---|
| Range of Molecular Weight | Peak Area Percentage %, λ 220 nm |
| >1500 | <1 |
| 1500~1300 | 7~8 |
| 1300~500 | 20~25 |
| 500~200 | 50~55 |
| <200 | <20 |

Range of Number-Average Molar Mass: 170~3000
Range of Weight-Average Molar Mass: 180~4000.

(8) The content of the peptide obtained by the method is more than 80 wt %, in which more than 95% of the walnut peptide has a molecular weight of less than 1500 Dalton, which is a high-purity, low-molecular-weight oligopeptide.

DETAILED DESCRIPTION

The present invention is further described by the following examples. It should be understood that, the method disclosed by the example of the invention is only used for explaining the invention and is not limited by the invention. On the premise of the conception of the invention, the simple improvement of the preparation method of the invention belongs to the protection scope of the invention. All the raw materials and solvents used in the examples are not specifically described, and are commercially available products.

Preparation Example 1

Figure 1:
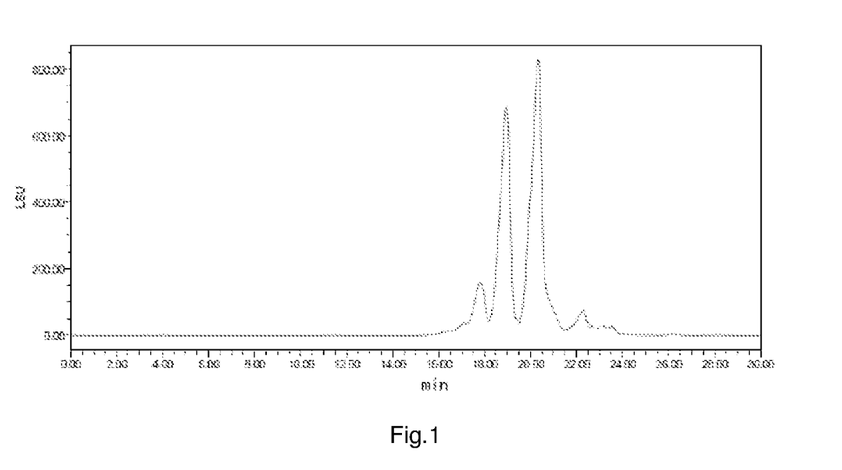
FIG. 1: A liquid chromatogram of the walnut oligopeptide of Preparing Example 1.

100 kg of walnut residue which was subjected to cold pressing and degreasing (recorded as A) was mixed with water according to a weight ratio of 1:10, adjusting the pH value to 10, and extracting for 2 hours at the room temperature; filtrating was carried out after the extraction. The filter residue was subjected to secondary extraction, and the filtrate was poured into an equal amount of walnut residue (recorded as B), adjusting the pH value to 10, and extracting for 2 hours at room temperature; and B, completing the first extraction, the filtrate was to be used, and the filter residue continued to be extracted for the second time; after A was carried out the secondary extraction, the filter residue was abandoned, and the filtrate was poured into an equal amount of walnut residue (recorded as C), adjusting the pH value to 10, and extracting for 2 hours at the room temperature; and after B was carried out the secondary extraction, removing the filter residues, and the filtrate was poured into the filter residue extracted in the first time for extracting for 2 hours, and the filtrate for C extracted by the first time was to be used; the sample C was extracted for the second time, discarding the filter residue, and the filtrate for later use; finally, combining the filtrate to be used, adjusting the pH value to be 5, and standing for 6 hours, removing the supernatant, finally adding water with the volume ratio of 1:10 into the precipitate, and uniformly stirring. The walnut protein solution was heated to 45° C., and the pH value was adjusted to be neutral, adding 1 kg of neutral protease (enzyme activity is 300,000 u/g) after enzymolysis was carried out for 6 hours, boiling inactivation was carried out for 30 minutes, and centrifugation was carried out, the supernatant was a enzymatic proteolysate liquid. The enzymatic proteolysate liquid was filtered by using a micro-filtration membrane with the pore size of 0.1 μm, the permeation liquid was treated by a 5000 Dalton ultrafiltration membrane, the penetrating liquid was concentrated at the temperature of 80° C. until the solid content reached 3.4%, spray drying was carried out, and the inlet temperature was 140° C., and the outlet temperature was 55-65° C. to obtain the light yellow walnut peptide powder with high purity and low molecular weight, the yield was 21%. The GB/T 22492-2008 appendix A and appendix B detection methods were adopted, the measured peptide content was 81 wt %, 97% of them has a molecular weight of less than 1500 Dalton, and the molecular weight distribution was as described above. The content result of the peptide is as follows:

Test Result

| Test Item | Unit | Test Method | Test Result 003 | Detection Limit of Method |
|---|---|---|---|---|
| peptide content | g/100 g | GB/T 22492-2008 Appendix B | 81.0 | — |
| Mesonin | g/100 g | GB/T 22492-2008 Appendix B | 86.7 | — |
| L-aspartic acid | g/100 g | GB/T 22492-2008 | 0.05 | 0.01 |
| L-threonine | g/100 g | GB/T 22492-2008 | 0.07 | 0.01 |
| serine | g/100 g | GB/T 22492-2008 | 0.25 | 0.01 |
| glutamic acid | g/100 g | GB/T 22492-2008 | 0.27 | 0.01 |
| glycine | g/100 g | GB/T 22492-2008 | 0.08 | 0.01 |
| L-alanine | g/100 g | GB/T 22492-2008 | 0.40 | 0.01 |
| L-cystine | g/100 g | GB/T 22492-2008 | 0.29 | 0.01 |
| L-valine | g/100 g | GB/T 22492-2008 | 0.23 | 0.01 |
| L-methionine | g/100 g | GB/T 22492-2008 | 0.04 | 0.01 |
| L-isoleucine | g/100 g | GB/T 22492-2008 | 0.22 | 0.01 |
| L-leucine | g/100 g | GB/T 22492-2008 | 0.63 | 0.01 |
| L-tyrosine | g/100 g | GB/T 22492-2008 | 0.53 | 0.01 |
| phenylalanine | g/100 g | GB/T 22492-2008 | 1.79 | 0.01 |
| lysine | g/100 g | GB/T 22492-2008 | ND | 0.01 |
| L-histidine | g/100 g | GB/T 22492-2008 | 0.16 | 0.01 |
| L-tryptophan | g/100 g | GB/T 22492-2008 | 0.14 | 0.01 |
| L-arginine | g/100 g | GB/T 22492-2008 | 0.99 | 0.01 |
| L-proline | g/100 g | GB/T 22492-2008 | ND | 0.01 |
| Total | g/100 g | GB/T 22492-2008 | 6.14 | 0.01 |

Preparation Example 2

Figure 2:
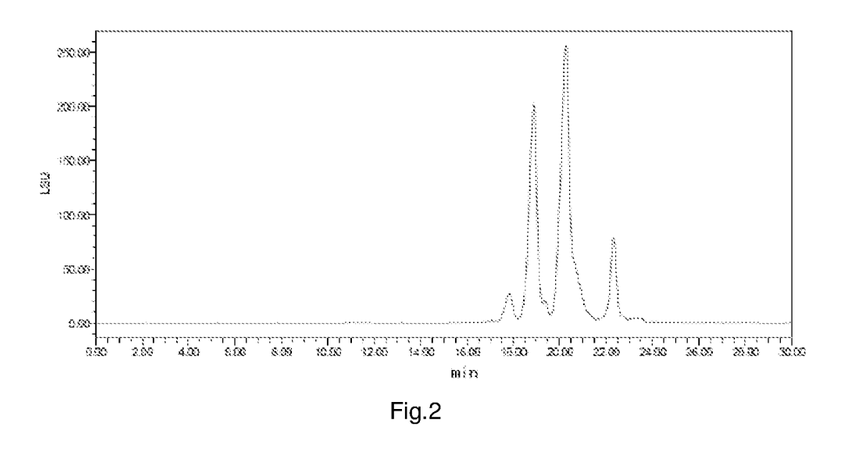
FIG. 2: A liquid chromatogram of the walnut oligopeptide of Preparing Example 2.

100 kg of walnut residue which was subjected to cold pressing and degreasing (recorded as A) was mixed with water according to a weight ratio of 1:10, adjusting the pH value to 10, and extracting for 2 hours at the room temperature; filtrating was carried out after the extraction, the filter residue was subjected to secondary extraction, and the filtrate was poured into an equal amount of walnut residue (recorded as B), adjusting the pH value to 10, and extracting for 2 hours at room temperature; and after the first extraction of B, the filtrate was to be used, and the filter residue continued to be extracted for the second time; after the secondary extraction was completed, the filter residue was abandoned, and the filtrate was poured into an equal amount of walnut residue (recorded as C), adjusting the pH value to 10, and extracting for 2 hours at the room temperature; and B was carried out the secondary extraction, removing the filter residues, and the filtrate was poured into the filter residue extracted in the first time for extracting for 2 hours, and the filtrate extracted by the first time was to be used; the sample C was extracted for the second time, discarding the filter residue, and filtrating the filtrate for later use; finally, combining the filtrate to be used, adjusting the pH value to be 5, and standing for 6 hours, removing the supernatant, finally adding water with the volume ratio of 1:10 into the precipitate, and uniformly stirring. The walnut protein solution was heated to 45° C., and the pH value was adjusted to be neutral, adding 1 kg of complex enzyme of neutral protease and papain with the weight of the walnut residue (in which the mass ratio of the two proteases was 1:1, the activity of neutral protease was 300,000 u/g, and the activity of papain is 500,000 u/g). After enzymolysis was carried out for 6 hours, boiling inactivation was carried out for 30 minutes, and centrifugation was carried out, the supernatant was an enzymatic proteolysate liquid, and the enzymatic proteolysate liquid was filtered by using a micro-filtration membrane with the pore size of 0.1 μm, the permeation liquid was treated by a 5000 Dalton ultrafiltration membrane, the penetrating liquid was concentrated at the temperature of 80° C. until the solid content reached 4.1%, spray drying was carried out, and the inlet temperature was 140° C., and the outlet temperature was 55-65° C. to obtain the light yellow walnut peptide powder with high purity and low molecular weight, the yield was 21 wt %. By applying Methods GB/T 22492-2008, Appendix A and Appendix B, and the measured peptide content was 81.3 wt %, 96% of them has a molecular weight of less than 1500 Dalton, and the molecular weight distribution was as described above. The results of the peptide content after enzymolysis of the complex enzyme of neutral protease and papain are as follows:

| Test Item | Unit | Test Method | Test Result 004 | Detection Limit of Method |
|---|---|---|---|---|
| peptide content | g/100 g | GB/T 22492-2008 Appendix B | 81.3 | — |
| L-aspartic acid | g/100 g | GB/T 22492-2008 | 0.13 | 0.01 |
| L-threonine | g/100 g | GB/T 22492-2008 | 0.11 | 0.01 |
| serine | g/100 g | GB/T 22492-2008 | 0.32 | 0.01 |
| glutamic acid | g/100 g | GB/T 22492-2008 | 0.44 | 0.01 |
| glycine | g/100 g | GB/T 22492-2008 | 0.43 | 0.01 |
| L-alanine | g/100 g | GB/T 22492-2008 | 0.52 | 0.01 |
| L-valine | g/100 g | GB/T 22492-2008 | 0.21 | 0.01 |
| L-methionine | g/100 g | GB/T 22492-2008 | 0.08 | 0.01 |
| L-isoleucine | g/100 g | GB/T 22492-2008 | 0.15 | 0.01 |
| L-leucine | g/100 g | GB/T 22492-2008 | 0.79 | 0.01 |
| L-tyrosine | g/100 g | GB/T 22492-2008 | 0.61 | 0.01 |
| phenylalanine | g/100 g | GB/T 22492-2008 | 1.24 | 0.01 |
| lysine | g/100 g | GB/T 22492-2008 | 0.66 | 0.01 |
| L-histidine | g/100g | GB/T22492-2008 | 0.13 | 0.01 |
| L-arginine | g/100 g | GB/T 22492-2008 | 1.29 | 0.01 |
| L-proline | g/100 g | GB/T 22492-2008 | ND | 0.01 |
| Total of 16 Amino acids | g/100 g | GB/T 22492-2008 | 7.11 | 0.01 |
| Mesonin | g/100 g | GB/T 22492-2008 Appendix B | 88.4 | — |

Preparation Example 3

Preparation of Composition

The acceptable additives in the medicines or food include but not limited to any adjuvant, carrier, excipient, flow aid, sweetening agent, diluent, preservative, dye/colorant, fragrance enhancer, surfactant, wetting agent, dispersing agent, suspending agent, stabilizer, isoosmotic pressure agent, solvent, an emulsifier, or the like, which have been recognized by US Food And Drug Administration, can be used for humans or animals, and does not have any side effect on the composition pharmaceutical composition.

Those skilled in the art may readily mix the walnut oligopeptide powder with the above additive agent according to any known method in the prior art and any dosage form known in the prior art.

Biological Activity Example 1

1. DPPH Free Radical Scavenging Experiment:

1.1 Preparation of DPPH ethanol solution: precisely weighing 4 mg of walnut oligopeptide powder, putting into a 100 ml brown volumetric flask, and adding 50 ml of ethanol, the ultrasonic treatment was carried out for 30 seconds, ethanol was used for fixing the volume to scale, shaking, and the product needs to be freshly prepared when needed.

1.2 Preparation of test solution: precisely weighing 10 mg of walnut oligopeptide powder, and putting into a 50 ml brown volumetric flask, adding 30 ml of ethanol, carrying out ultrasonic treatment for 5 minutes, diluting with ethyl alcohol for fixing the volume to scale, and shaking.

1.3 Operation steps: accurately sucking 2 ml of test solution and 2 ml of DPPH solution, and uniformly mixing; accurately sucking 2 ml of test solution and 2 ml of ethanol, and uniformly mixing; accurately sucking 2 ml of DPPH solution and 2 ml of ethanol, uniformly mixing, and standing at room temperature for 30 minutes, the absorbance was measured at the wavelength of 515 nm, and the removal rate of the free radicals was calculated according to the following calculation formula:

$$IR\% = [1-(Ai-Aj)/A0]*100\%;$$

in which, Ai represents the absorbance of the mixture of the test solution and DPPH, Aj represents the absorbance of the mixture of the test solution and solvent, and A0 represents the absorbance of the mixture of DPPH and solvent.

2. ABTS$^+$ Free Radical Scavenging Experiment:

2.1 Preparation of PBS buffer solution: weighing 8 g of sodium chloride, 0.2 g of potassium chloride, 0.24 g of monopotassium phosphate, and 3.62 g of disodium hydrogen phosphate dodecahydrate and putting them into a 1000 ml beaker, adding 800 ml of distilled water, stirring to dissolve, and adjusting the pH value to 7.4 by using hydrochloric acid or sodium hydroxide, transferring into a 1000 ml volumetric flask, adding distilled water to dilute, shaking evenly, and standing for later use.

2.2 Preparation of ABTS$^+$ storage solution: precisely weighing 78 mg of ABTS$^+$ and put into a 20 ml brown volumetric flask, 15 ml of distilled water was added, the mixture was subjected to ultrasonic treatment for 5 min, and distilled water was used for constant volume to the scale, shaking up and precisely weighing 76 mg of potassium persulfate, putting into a 2 ml brown volumetric flask, adding 1 ml of distilled water, dissolving the distilled water in an ultrasonic manner, and fixing the volume with distilled water until the scale was reached, uniformly shaking. 352 μL potassium persulfate solution was added into the ABTS solution, shaking uniformly, standing overnight.

2.3 Preparation of ABTS$^+$ working solution: precisely sucking 1 mL of storage solution, adding 65 mL of PBS buffer solution, and shaking uniformly.

2.4 Preparation of test solution: precisely weighing 20 mg of walnut oligopeptide powder, and putting into 20 ml brown flask, adding 15 ml of PBS buffer solution, and carrying out ultrasonic treatment for 5 minutes, PBS buffer solution was used for constant volume to the scale, and shaking uniformly.

2.5 Operation steps: accurately sucking 0.5 ml of test solution and 5 ml of ABTS working solution, and mixing uniformly; accurately sucking 0.5 ml of test solution and 5 ml of PBS buffer solution, and mixing uniformly; accurately sucking 5 ml of ABTS working solution and 0.5 ml of PBS buffer solution, and mixing uniformly, the absorbance was measured immediately at 734 nm, and the free radical removal rate was calculated according to the following formula:

$$IR\% = [1-(Ai-Aj)/A0]*100\%;$$

in which, Ai represents the absorbance of the mixture of the test solution and ABTS, Aj represents the absorbance of the mixture of the test solution and solvent, and A0 represents the absorbance of the mixture of ABTS and solvent.

3. SRSA Superoxide Anion Free Radical Scavenging Experiment:

3.1 Preparation of 0.1 moL/L PBS buffer solution (pH 7.4): 80 g of sodium chloride, 2 g of potassium chloride, 2.4 g of monopotassium phosphate and 23.1 g of dipotassium hydrogen phosphate trihydrate were weighted and placed in 1000 ml beaker, adding 600 ml of distilled water, stirring to dissolve, and adjusting the pH to 7.2 with hydrochloric acid or sodium hydroxide, transferring into 1000 ml volumetric flask, adding distilled water to dilute to the scale, shaking evenly, and standing for later use.

3.2 Preparation of 150 μmoL/L NBT solution: accurately weighing 12.5 mg of NBT and putting into 100 mL brown volumetric flask, adding distilled water, dissolving by ultrasonic waves, diluting with distilled water to the scale, and uniformly shaking.

3.3 Preparation of 60 μmoL/L PMS solution: accurately weighing the PMS 18.8 mg and putting into 1000 ml volumetric flask, adding distilled water, dissolving by ultrasonic waves, diluting with distilled water to the scale, and uniformly shaking.

3.4 Preparation of 468 μmoL/L NADH solution: accurately weighing the NADH 33.9 mg and putting into 100 ml volumetric flask, adding distilled water, dissolving by ultrasonic waves, diluting with distilled water to the scale, and uniformly shaking.

3.5 Preparation of test solution: preparing 1 mg/ml of walnut oligopeptide powder to be tested.

3.6 Preparation of working solution: 1 ml of 0.1 mol/l PBS buffer solution (pH 7.4) was added into volumetric flask, adding 1 ml of 150 μmoL/L NBT solution, 2 ml of 468 μmol/l NADH solution and 1 ml of 60 μmoL/L of PMS solution, and uniformly stirring, reacting at the temperature of 25° C. for 5 minutes, and measuring the absorbance value at the wavelength of 560 nm.

3.7 Operation steps: accurately sucking 0.5 ml of test solution and 5 ml of the working solution, and uniformly mixing; accurately sucking 0.5 ml of test solution and 5 ml of distilled water, and uniformly mixing; accurately sucking 5 ml of the working solution and 0.5 ml of distilled water, and uniformly mixing, the absorbance was determined immediately at 560 nm, and the free radical scavenging rate was calculated according to the following formula:

$$IR\% = [1-(Ai-Aj)/A0]*100\%;$$

in which, Ai represents the absorbance of the mixture of the test solution and ABTS, Aj represents the absorbance of the mixture of the test solution and the solvent; and A0 represents the absorbance of the mixture of SRSA and solvent.

The proteolysis product by the neutral protease in the preparation example 1 was prepared in a concentration of 100 μg/mL, in which the Vitamin C is used as a positive control (in a concentration of 100 μg/mL), and the test result is shown in Table 1:

TABLE 1

Antioxidant Activity of Walnut Oligopeptide Powder

| Test Sample | DPPH scavenging rate % | ABTS+ scavenging rate % | SRSA scavenging rate % |
|---|---|---|---|
| Preparation Example 1 | 82.5 | 79.2 | 56.8 |
| Preparation Example 2 | 87.3 | 83.4 | 62.3 |
| Vitamin C | 97.2 | 98.1 | 80.1 |

It can be seen from Table 1, the walnut oligopeptide powder prepared by the method of the present invention has a relatively strong scavenging activity on DPPH and ABTS free radicals and a medium strength of scavenging activity of on the superoxide anion. Therefore the antioxidant activity is better.

Biological Activity Example 2

PC12 nerve cell protection model: This is a good model for studying nerve cell physiology, pathology and pharmacology, and also a most common in-vitro drug screening model for studying Parkinson's disease and neuro-fatigue.

1. Culturing of PC12 Cells

PC12 cells were cultured by using a high-sugar DMEM culture medium containing 10% fetal calf serum, and digesting for about 50 seconds by using 0.25% of pancreatin during cell passage, stopping digestion by using a DMEM culture medium containing 10% serum, and adding fresh culture medium to blow the cells uniformly. Cell density passage of $10^5$/ml was carried out. 4 ml of culture solution containing cells was added to each bottle of cells, culturing under the conditions of 37° C. and 5% $CO_2$.

2. Cell Inoculation

The PC12 cells grew to fusion state in a culture bottle, and were digested by using 0.25% trypsin solution, and repeatedly blowing to the cell suspension, diluting into $1.0\times10^5$/mL with the high-sugar DMEM culture medium containing 10% FBS, 100 μL of each hole is inoculated into 10 complex holes in each group of 96-well culture plates, and culturing for 24 hours under the conditions of 37° C. and 5% $CO_2$, fusion state was obtained.

3. The Influence of the Drug on the Normal PC12 Cell Growth Activity

The 96-well plate was respectively given to 100 μL of the walnut oligopeptide by a certain concentration gradient in each hole, after culturing for 24 hours, the cell vitality was detected by MTT method. 50 mg of MTT was dissolved in 10 ml of PBS and was filtered by 0.22 μm microfiltration membrane. Before being used, it was diluted to 0.5 mg/ml, and culture medium of the each group cell was abandoned, washed twice with PBS. 0.5 mg/ml of MTT was added, carrying out incubation for 3 hours under the conditions of 37° C. and 5% $CO_2$, removing the MTT working solution, and adding 150 μL DMSO into each hole to dissolve, shaking for 10 min, measuring the OD value of each hole (the measurement wavelength was 570 nm, and the reference wavelength was 650 nm). The cell activity of the model group and the drug delivery group was calculated by taking the average value of the OD value of the control group as 100% of the cell activity. The measurement results are shown in Table 2.

TABLE 2

The Influence of Walnut Oligopeptide Powder on Normal PC12 Cell Activity

| Group | Concentration (μg/ml) | Cell Activity (%) |
|---|---|---|
| Control | | 100.0 ± 4.7 |
| | 0.1 | 101.2 ± 4.6 |
| | 1 | 100.4 ± 5.3 |
| | 10 | 103.4 ± 9.2 |
| | 30 | 99.7 ± 7.8 |
| Preparation Example 1 | 100 | 99.6 ± 5.5 |
| | 200 | 100.7 ± 6.6 |
| | 300 | 106.0 ± 5.3 |
| | 400 | 105.5 ± 6.2 |
| | 500 | 103.8 ± 7.8 |
| | 1000 | 101.0 ± 5.5 |

4. Protection Effect of the Drug on PC12 Cell by Hydrogen Peroxide Damage (Detecting Whether the Drug Can Remove Free Radicals in the Cells to Promote the Growth of the Cells)

A. Blank group (DMEM for 1% serum).

B. Model group (1% serum DMEM was cultured for 6 hours, then adding $H_2O_2$ to enable the final concentration of the $H_2O_2$ to be 100 μM, and stimulating for 12 hours).

C. Positive drug (NAC) group: Adding 1% of serum DMEM containing positive drug of a certain concentration to culture for 6 hours, and then the mixture was added with 100 μM $H_2O_2$ to stimulate for 12 hours.

D. Administration group: Adding DMEM for 1% serum of the walnut oligopeptide with the concentration gradients to culture for 6 hours, and then the mixture was added with 100 μM $H_2O_2$ to stimulate for 12 hours.

The above groups were cultured under the same conditions, and then subsequent experiments were carried out. The cell activity was detected by MTT method in 96-well plates. The measurement results are shown in Table 3.

TABLE 3

The Influence of the Walnut Oligopeptide Powder on the $H_2O_2$ induced PC12 cell by oxidative damage

| Group | Concentration (μg/ml) | Cell activity(%) |
|---|---|---|
| Control group | | 100.0 ± 4.8 |
| Model group | | 57.2 ± 6.5 |
| Positive group | 80 | 88.0 ± 3.3 |
| Preparation Example 1 | 0.1 | 57.9 ± 4.8 |
| | 1 | 56.0 ± 3.7 |
| | 10 | 66.7 ± 3.2 |
| | 30 | 67.9 ± 5.3 |
| | 100 | 66.9 ± 3.1 |
| | 200 | 76.9 ± 6.0 |
| | 300 | 76.0 ± 5.2 |

TABLE 3-continued

The Influence of the Walnut Oligopeptide Powder on the $H_2O_2$ induced PC12 cell by oxidative damage

| Group | Concentration (μg/ml) | Cell activity(%) |
|---|---|---|
| | 400 | 74.8 ± 10.0 |
| | 500 | 72.0 ± 4.8 |

As can be seen from Table 2, the walnut oligopeptide powder in the invention does not reduce the proliferation activity of PC12 cells, and the number of the PC12 cells is remarkably increased along with the improvement of the concentration. As can be seen from Table 3, the cell activity of the model group is 57.2% after the stimulation of $H_2O_2$, and; after 80 μg/mL of the positive control medicine was added for culturing, the cell activity is increased to 88.0%, achieving a significant protection effect. After the walnut oligopeptide was added, the cell activity is increased along with the increasing concentration of the peptide powder, the concentration dependence is presented, and the protection effect is significant. When the concentration was 500 μg/mL, the cell activity reached 72.0%, and the cell activity increased by 30% as compared with the Model group. So the peptide powder has a relatively strong protection effect on neuronal cells, so that it can be used in drugs or health-care foods for preventing or treating Parkinson's disease, Alzheimer's disease, similar diseases, and for relieving brain fatigue.

Biological Activity Example 3

Figure 3:
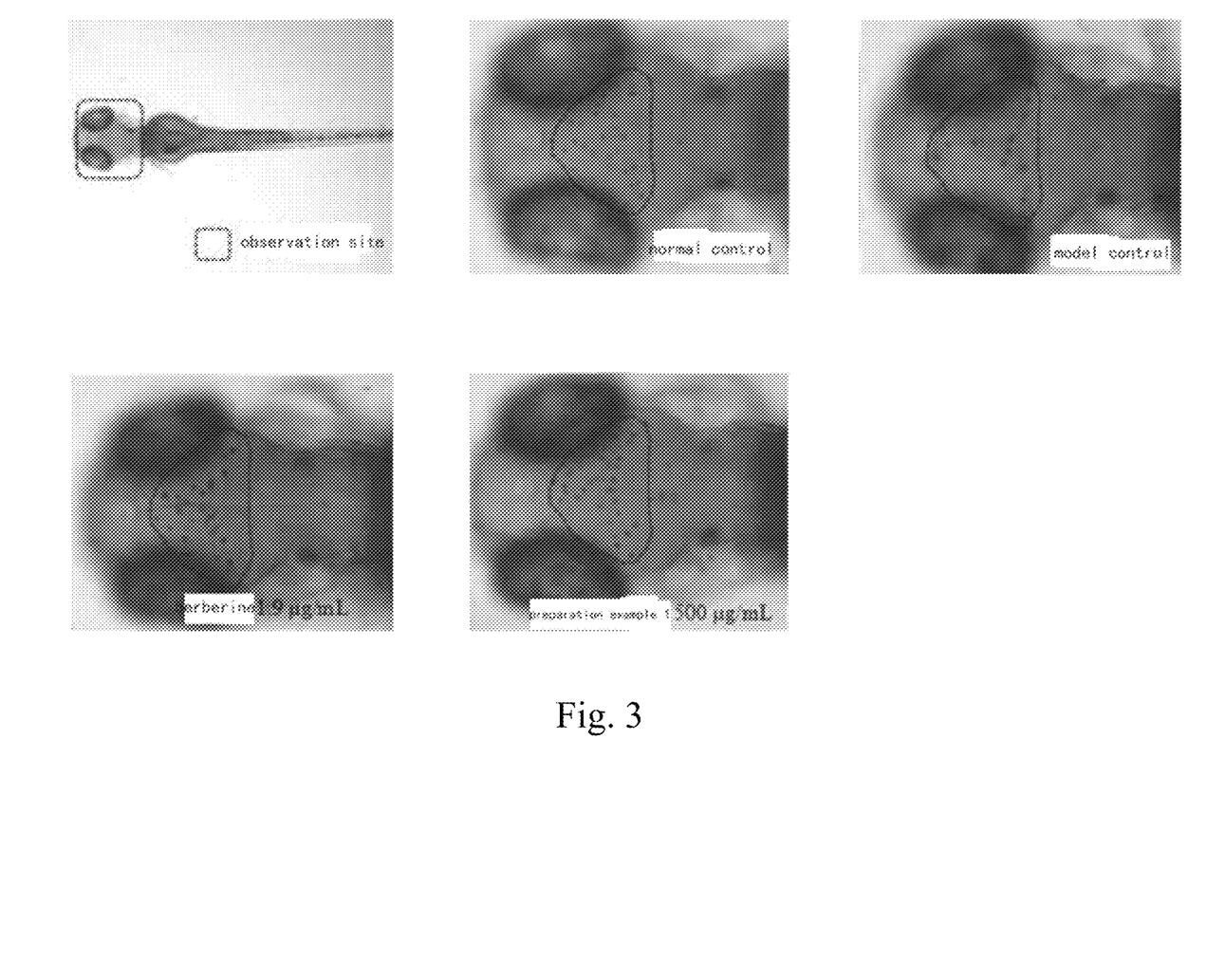
FIG. 3: Improved effect diagram of walnut oligopeptide on zebra fish macrophage inhibition.

Improvement Effect of Walnut Oligopeptide Powder on Inhibition of Zebra Fish Macrophages Zebra fish macrophage inhibition model was built by intravenous injection of vinorelbine in 2 days (2 dpf) zebra fishes after fertilization, respectively dissolving the walnut oligopeptide powder and the positive control drug berberine in fish water, and the concentration of the oligopeptide powder was 500 μg/mL, and the concentration of the berberine was 1.9 μg/mL; Meanwhile, model control group and normal control group were set (no treatment was carried out), in which 30 tail zebra fishes were in each experimental group, and each group was placed in a 28 L incubator to be cultured. When processing to 3 dpf, the zebra fishes in each experiment group were subjected to neutral red staining. After dyeing for 4 hours, 10-tail zebra fishes from each experimental group were selected to be observed under microscope randomly, and photos were taken and stored. Image analysis for the number of the zebra fish macrophages was carried out by image processing software. The improvement effect of the walnut oligopeptide powder on inhibition of the zebra fish macrophage was quantitatively evaluated.

TABLE 4

The Improvement Effect of the walnut oligopeptide powder on Macrophage of the Zebra Fish Head (n = 10)

| Group | Concentration (μg/mL) | Mean ± SD(count) | Improvement Effect (%) |
|---|---|---|---|
| Normal control group | | 27 ± 4 | — |
| Model control group | | 15 ± 3 | — |
| Berberine | 1.9 | 20 ± 4 | 41.67 |
| Preparation Example 1 | 500 | 25 ± 4 | 83.33 |

As can be seen from Table 4, the average number of macrophages in the normal control group zebra fishes is 27. Compared with model control group (15), the zebra fish macrophage inhibition model was established successfully. When the concentration of the positive drug berberine is 1.9 μg/mL, the average number of macrophages is 20, and compared with the model control group (15) and the improvement effect on inhibition of zebra fish macrophage is 41.67%. It shows that it has an significant improvement effect on the inhibition of the zebra fish macrophage. When the concentration of walnut oligopeptide powder is 500 μg/mL, the average number of macrophages is 25, compared with the model control group (15), the improvement effect on inhibition of zebra fish macrophage is 83.33%, showing that the walnut oligopeptide powder disclosed in the invention has an significant improvement effect on inhibition of zebra fish macrophage cells.

Figure 4:
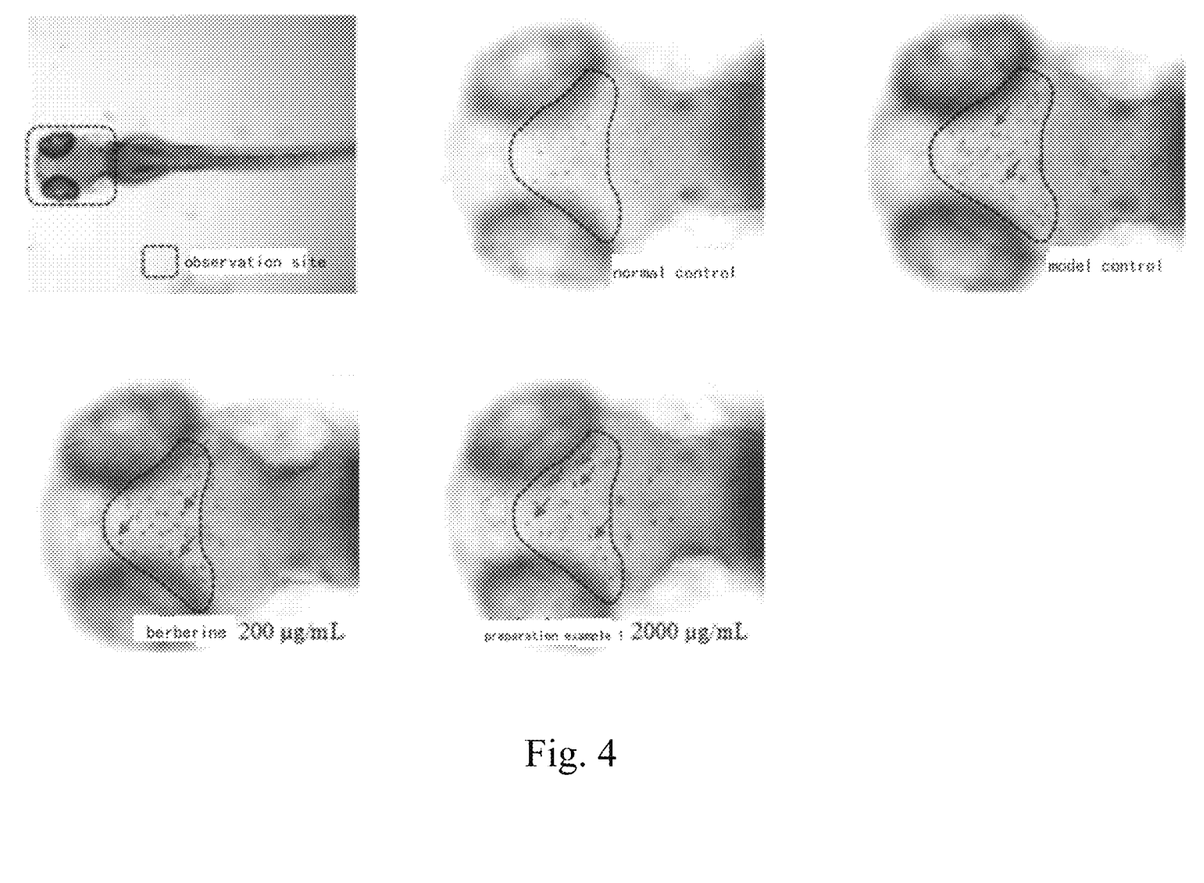
FIG. 4: Promoting effect diagram of walnut oligopeptide to zebra fish macrophage phagocytosis function.

2. Promotion Effect of Walnut Oligopeptide Powder on Phagocytosis Function of Zebra Fish Macrophages Zebra fish macrophage promoting model inhibition model was built by intravenous injection of ink in 2 days (2 dpf) zebra fishes after fertilization. respectively dissolved in fish water to give the walnut oligopeptide and the positive drug pidotimod, the concentration of the oligopeptide was 2000 μg/mL, and the concentration of the pidotimod is 200 mg/mL. Meanwhile, model control group and normal control group were set, in which 30 tail zebra fishes are in each experimental group, and each group was placed in a 28 L incubator to be cultured. When processing to 3 dpf, the zebra fishes in each experiment group were subjected to neutral red staining, after dyeing for 4 hours, 10-tail zebra fishes from each experimental group were selected to be observed under microscope randomly, and photos were taken and stored; image analysis for the ink signal of the zebra fish macrophages was carried out by image processing software. The improvement effect of four test samples on phagocytosis function of the zebra fish macrophages was quantitatively evaluated.

TABLE 5

The Promotion Effect of Walnut Oligopeptide Powder on Macrophages of Zebra Fish Head Phagocytosis Ink (n = 10)

| Group | Concentration (μg/mL) | Mean ± SD(count) | Promotion Effect (time) |
|---|---|---|---|
| Model control group | | 1.5 ± 1.3 | — |
| pidotimod | 200 | 3.5 ± 1.8 | 2.3 |
| Preparation Example 1 | 2000 | 5.1 ± 2.1 | 3.4 |

As can be seen from Table 5, when the concentration of the positive drug pidotimod is 200 μg/mL, the average number of macrophages of the phagocytosis ink is 3.5. Compared with model control group (1.5), the promotion effect on the phagocytosis of the zebra fish macrophages is 2.3 times, showing that it has an significant improvement effect on the phagocytosis function of the zebra fish macrophages. When the concentration of the walnut oligopeptide is 2000 μg/mL, the average number of macrophages of the phagocytosis ink is 5.1. Compared with the model control group (1.5), the promotion effect on the phagocytosis of the zebra fish macrophages is 3.4 times, so that the walnut oligopeptide powder has a remarkable promoting effect on the phagocytosis function of the zebra fish macrophages.

Biological Activity Example 4

Figure 5:
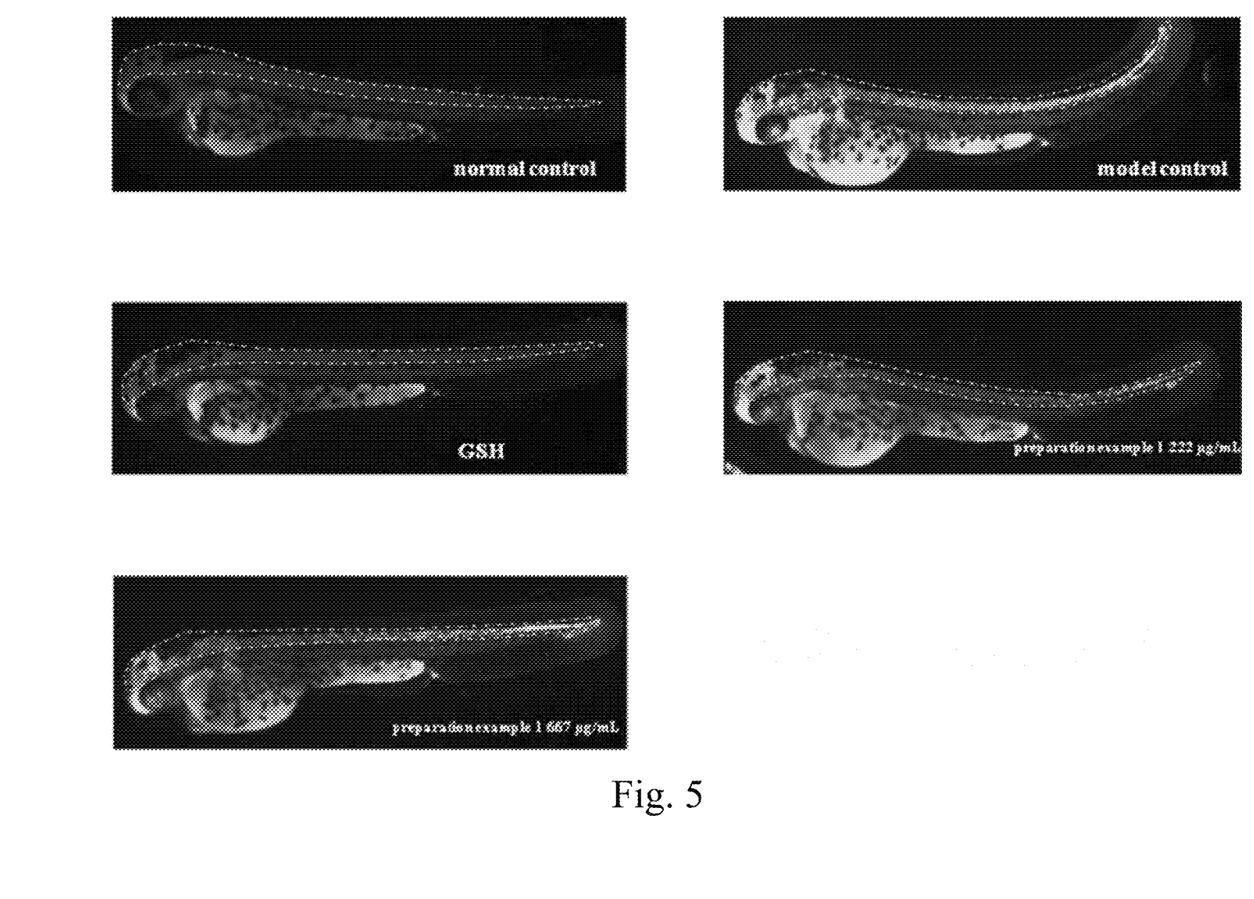
FIG. 5: Typical graph of walnut oligopeptide on the central nervous influence of zebra fishes.

Protection Effect of the Walnut Oligopeptide Powder on the Central Nervous Centrum of Zebra Fishes 180 wild type AB strain zebra fishes after fertilization in 16 days (1 dpf) were selected randomly and were arranged in six-well plate, and 30 tail zebra fishes were treated in each hole (the experiment group), and central injury of the zebra fishes was induced by the mycophenolate mophol ester. When the concentration of low-polypeptide powder in water was 222 and 667 μg/mL respectively, the concentration of positive control drug glutathione (GSH) was 154 μg/mL, meanwhile normal control group (zebra fish treated by water raising for fish) and model control group were set, in which the capacity of each hole (the experiment group) was 3 ml. After the oligopeptide was subjected to co-treatment for 24 hours with the mycophenolate, the acridine orange was used for dyeing, after dyeing, 10 tail zebra fishes from each experimental group were selected randomly to photograph under fluorescence microscope and collect data, analyzing and counting the fluorescent intensity of the apoptotic cells of central nervous system (brain and spinal cord) of the zebra fishes; the protective effect of the walnut oligopeptide powder on the central nervous system of zebra fishes was evaluated according to the fluorescence intensity.

TABLE 6

Protection Effect of Walnut Oligopeptide Powder on Central Nervous System of Zebra Fishes (n = 10)

| Group | Concentration (μg/mL) | fluorescence intensity of central apoptosis cell (pixel)(mean ± SE) | Protection Effect on Central Nervous System (%) |
|---|---|---|---|
| normal control group | — | 161976 ± 5881 | — |
| model control group | — | 565783 ± 14621 | — |
| GSH | 154 | 193900 ± 8302 | 92 |
| Preparation Example 1 | 222 | 395025 ± 22425 | 42 |
| | 667 | 451259 ± 18521 | 28 |

As shown in Table 6, by comparing the fluorescence intensity of the central nervous apoptosis cells of zebra fishes in the model control group (565783 pixels) and the normal control group (161976 pixels), it can be seen that the model was established successfully. The fluorescence intensity of the central nervous apoptosis cells of the zebra fishes with the concentration of GSH 154 μg/mL of the positive control drug is 190000 pixels. Compared with model control group, the protection effect on the central nervous system of the zebra fishes is 92%, showing that the GSH has an significant protection effect on the central nervous system of the zebra fishes. The fluorescent intensity of central nervous apoptosis cells of the zebra fish with the concentration of 222 and 667 μg/mL is 395025 and 451259 pixels respectively, and the central nervous protection effect is 42% and 28% respectively. Compared with the model control group, the walnut oligopeptide has an significant protective effect on the central nervous centrum of the zebra fishes.

Biological Activity Example 5

1. The Improvement Effect of the Walnut Oligopeptide on the Movement Capability of the Zebra Fishes 4 dpf wild type AB strain zebra fish were selected randomly and were arranged in a six-hole plate, in which 30 tails in each hole (namely each test sample set), the walnut oligopeptide and the positive control medicine (Chinese stroke pill) in water with the concentration of 1.0 mg/mL were respectively administrated, meanwhile normal control group and model control group were arranged, and the capacity of each hole was 3 ml. After the test product was preprocessed for a period of time, the rest of the experimental groups were simultaneously administrated the sodium sulfite in water to induce zebra fish fatigue model except the normal control group. The zebra fish was jointly processed with test product and sodium sulfite for a period of time. 10-tail zebra fishes were selected in each experimental group randomly, and behavior analysis was carried out, measuring the total movement distance of the zebra fishes. The movement improvement effect of the test product on the fatigue of zebra fishes induced by sodium sulfite was evaluated quantitatively.

2. Influence of Walnut Oligopeptide on Lactic Acid Metabolism in Zebra Fish 4 dpf wild type AB strain zebra fish were selected randomly and were arranged in a six-hole plate, in which 30 tails in each hole (namely each test sample set), the walnut oligopeptide and the positive control medicine (Chinese stroke pill) in water with the concentration of 1.0 mg/mL were respectively administrated, meanwhile normal control group and model control group were arranged, and the capacity of each hole was 3 ml. Three parallel test samples were arranged for each experiment group. After the test product was preprocessed for a period of time, the rest of the experimental groups were simultaneously administrated the sodium sulfite in water to induce zebra fish fatigue model except the normal control group. The zebra fish was jointly processed with test product and sodium sulfite for a period of time. The zebra fishes in three parallel experiment groups were gathered together (total 90 tails) and the content of lactic acid in the zebra fish body was measured indirectly by Nanodrop 2000 ultra-micro spectrophotometer. The effect of the walnut oligopeptide with the concentration of 2000 μg/mL on the content of lactic acid in the fatigue zebra fish body induced by sodium sulfite was evaluated quantitatively.

TABLE 7

Improvement Effect of Walnut Polypeptide on Movement Capability of Zebra Fishes

| Group | Concentration (μg/mL) | Total movement distance of zebra fishes (mm, Mean ± SE) | Improvement Effect of Movement Capability (%) |
|---|---|---|---|
| normal control group | | 11147 ± 564 | / |
| model control group | | 4285 ± 228 | / |
| Chinese stroke pill group | 1000 | 9878 ± 458 | 81.5 |

TABLE 7-continued

Improvement Effect of Walnut Polypeptide on Movement Capability of Zebra Fishes

| Group | Concentration (μg/mL) | Total movement distance of zebra fishes (mm, Mean ± SE) | Improvement Effect of Movement Capability (%) |
|---|---|---|---|
| Preparation Example 1 | 2000 | 10051 ± 462* | 84.0 |

TABLE 8

The Effect of the Walnut Polypeptide on the Content of Lactic Acid in Zebra Fish Body

| Group | Concentration (μg/mL) | Content of Lactic Acid in Zebra Fish (mmol/gprot) | Reduction rate of lactic acid content(%) |
|---|---|---|---|
| normal control group | | 0.297 ± 0.006 | / |
| model control group | | 0.794 ± 0.015 | / |
| Chinese stroke pill group | 1000 | 0.515 ± 0.008 | 56.1 |
| Preparation Example 1 | 2000 | 0.564 ± 0 | 46.4 |

As shown in Table 7 and Table 8, the walnut oligopeptide powder in the invention can significantly improve the movement capability of zebra fishes and improve the metabolism of lactic acid in the body. Therefore, the walnut oligopeptide powder has an obvious anti-fatigue effect and can be used in preparing foods, health-supplement or medicines for preventing or relieving fatigue.

Biological Activity Example 6

Inhibition Effect of Walnut Oligopeptide on $A\beta_{1-42}$ Amyloid Protein Aggregation The $A\beta_{1-42}$ amyloid protein was formulated to be 2.5 mg/mL in DMSO, and diluting the walnut oligopeptide powder to proper concentration. Then, $A\beta_{1-42}$ amyloid protein solution (1 μL) was mixed with the walnut oligopeptide solution (9 μL), so that the final concentration of the $A\beta_{1-42}$ amyloid protein was 0.25 mg/mL, and the final concentration of the walnut oligopeptide was 10 and 100 μg/mL. The mixed solution was reacted at 37° C. for 30 minutes, 200 μL of the final mixed solution was placed in transparent bottom and black 96-well plate, and the fluorescence intensity (Ex440/Em482) of ThT was measured from the bottom of the plate for determining the polymerization degree of the $A\beta_{1-42}$ amyloid protein. The negative control group does not have drug added.

TABLE 9

Inhibition Effect of Walnut Oligopeptide on $A\beta_{1-42}$ Amyloid Protein Aggregation

| Group | Concentration (μg/mL) | Inhibition effect(%) |
|---|---|---|
| Preparation Example 1 | 10 | 2.9 ± 4.2 |
| | 200 | 27.9 ± 2.9 |

As can be seen from Table 9, when the concentration of walnut oligopeptide is 10 μg/mL, the aggregation effect of the anti-$A\beta_{1-42}$ amyloid protein is not significant. When the concentration is 200 μg/mL, there is a certain inhibition effect on aggregation of the $A\beta_{1-42}$ amyloid protein. It is concluded that the walnut oligopeptide has protective effect on cranial nerves, and has potential effect of improving memory.

Biological Activity Example 7

Influence of Walnut Oligopeptide on Inflammatory Immune Factors in Cells

10 μg/mL of anti-CD3 was coated in 6-well plate (200 μL/well) and placed at the temperature of 4° C. for 18-24 hours. The HPBMC was activated, the cell suspension was used for diluting to $5 \times 10^5$ cells/mL, and the final volume was 36 ml, containing anti-CD28 (2 μg/mL), rhIL-2 (10 ng/mL), and rhIL-4 (50 ng/ml). The 6-well plate which has been coated with the anti-CD3 was flushed using culture medium, and transferring the HPBMC diluent to the 6-well plate, and culturing in a carbon dioxide incubator. After 2 days, the HPBMC diluent of the 6-well plate was collected and centrifuged, removing the supernatant, and then adding the culture medium containing rhIL-2 (10 ng/mL) and rhIL-4 (50 ng/ml), scattered and uniformly mixed, so that the concentration of the cells was $5 \times 10^5$ cells/mL, transferring to cell culture bottle, and then culturing in carbon dioxide incubator. After 2 days, the HPBMC was collected, supernatant was removed by centrifugation, and a cleaning with culture medium, centrifuging to remove supernatant again, adding culture medium containing 5 ng/ml of PMA, scattering and uniformly mixing, the cell concentration was $5 \times 10^5$ cells/mL, and the final volume was 36 ml, and was placed in carbon dioxide culture box for 4 hours. Centrifugation was carried out, and the supernatant was subjected to the CBA analysis. The operation method was carried out according to BD CBA Human Th1/Th2/Th17 Cytokine Kit Instruction Manual instruction, analyzing changes of IL-10 and IL-17A.

TABLE 10

Effect of Walnut Oligopeptide on IL-10 and IL-17A Factors in cell (n = 3)

| | | Cell Factors | |
|---|---|---|---|
| Group | Concentration (μg/mL) | Change of IL-10(%) | Change of IL-17A (%) |
| Negative Control | / | 100.0 ± 2.52 | 100.0 ± 3.75 |
| Preparation Example 1 | 100 | 81.5 ± 1.83 | 138.1 ± 3.72 |

As can be seen from Table 10, the walnut oligopeptide can significantly lower the content of IL-10, and the content of the IL-17A is increased. It can be seen that the walnut oligopeptide is able to adjust the inflammatory factors and increase the body immunity.

Biological Activity Example 8

Figure 6:
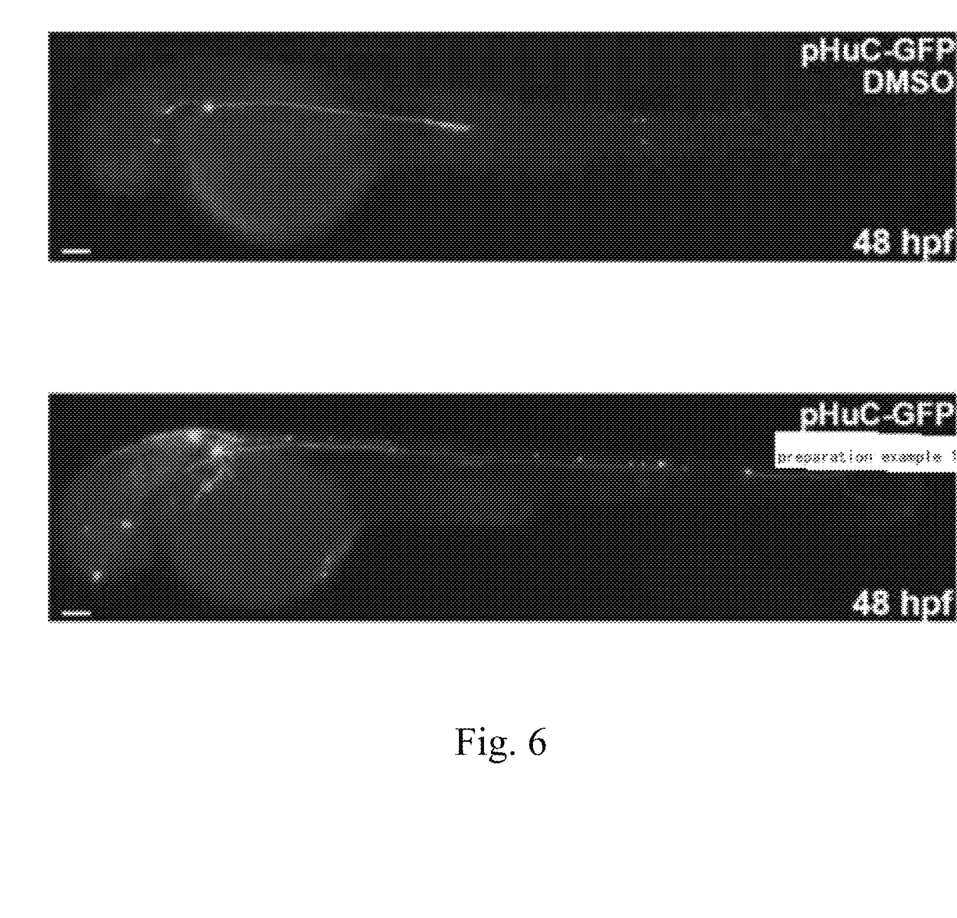
FIG. 6: Promotion effect diagram of walnut oligopeptide on growth of zebra fish embryo embryonic neurites.

1. The Promoting Effect of Walnut Oligopeptide on Growth of the Zebra Fish Embryo Nervous Process Green fluorescent fusion protein (GFP) was used as detection signal by utilizing nerve cell specific HuC promoter. The green fluorescent protein of the plasmid pHuC-GFP was firstly injected into cells of zebra fish embryo in 1-cell period. The walnut oligopeptide powder (Preparation Example 1) was dissolved with DMSO, and diluting with water to a certain concentration. After 8 hours, the mixture with DMSO (control negative) was injected into the zebra fish embryonic cells. After 40 hours, based on the number of the zebra fish nerve process, the promoting effect of the sample to the growth of the nerve process in the zebra fish embryo was determined.

Experimental results show that the growth promotion rate of the zebra fish embryo nervous process was only 23% as compared with negative DMSO group. After the injection of 1 mg/ml walnut oligopeptide, the growth promotion rate of the nerve process was 51%. It is significant that the walnut oligopeptide can promote the growth of the zebra fish embryo nerve process.

Figure 7:
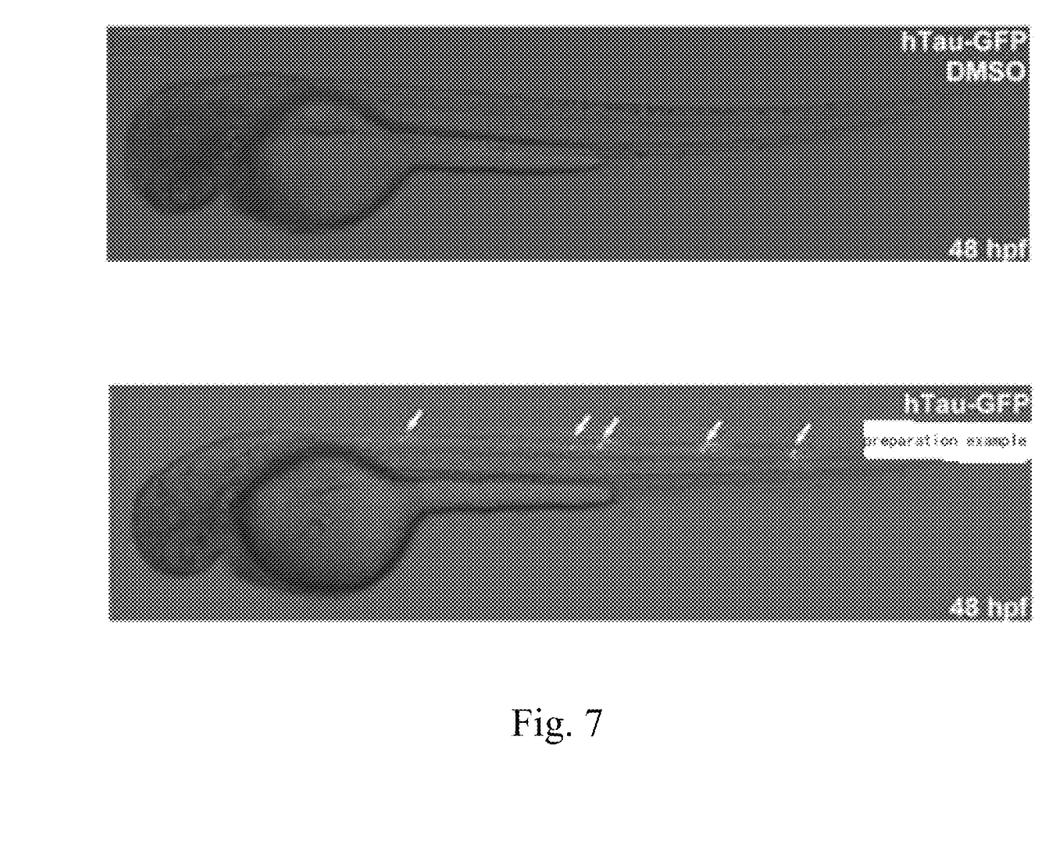
FIG. 7 is a graph showing reducing the toxicity of the human wild type tau protein to nerve cells in the zebra fish embryo by the walnut oligopeptide.

2. The Walnut Oligopeptide Reducing Toxicity of the Human Wild Type Tau Protein to Nerve Cells in the Zebra Fish Embryo By utilizing nerve cell specific HuC promoter, hTau green fluorescent fusion protein (GFP) was used for detecting the apoptosis condition of the nerve cells in the zebra fish embryo induced by the wild type human tau protein. The expression construct was injected into cells of a zebra fish embryo in a 1-cell period. The walnut oligopeptide powder (Preparation Example 1) was dissolved with DMSO, and diluting with water to a certain concentration. After 8 hours, the mixture with DMSO (control negative) was injected into the zebra fish embryonic cells. The conditions of 24 and 48 hpf GFP marked cells were observed by fluorescent microscope. Part of GFP signals can be observed in neuronal cells of the zebra fish 24 hpf, and part of those disrupt, and even disappear in neuronal cells of the zebra fish 48 hfs. The percentage composition of the zebra fish 48 hpf 3 to 5 GFP nerve cell cells was calculated.

Experimental results show that the control negative DMSO group only has 17.2% of GFP neuronal cells, and the walnut oligopeptide with the concentration of 1 mg/mL was injected, GFP neuronal cells can reach 37.6%. It is obvious that the walnut oligopeptide can reduce the toxicity of the human wild type tau protein to nerve cells in the zebra fish embryo.

In conclusion, the walnut oligopeptide has the effect of promoting or improving memory according to the two biological activity models.

Biological Activity Example 9

Effect of Walnut Oligopeptide on Chemical Drug-Induced Mouse Learning-Memory Disorders 1. Test Animal The test animal was a cleaning-grade ICR mouse with 18-22 g in weight, the three batches of 300 were provided by Nantong University. Laboratory animal production license is SCXK (Su) 2014-0001, fed by conventional mouse feedstuff, and free drinking water. Before the experiment they were fed in a quiet environment for 1 week, freely-feeding and drinking water, and keeping the room temperature (22±1° C.) and natural day and night rhythm illumination.

2. Experiment Method 2.1 Influence on Scopolamine-Induced Memory Acquisition Impairment of Mouse The mouse was randomly grouped and low, medium and high dosage groups (30, 100 and 300 mg/kg) of walnut oligopeptide (preparation example 1) was provided, the blank group and the model group were given equal-volume distilled water respectively, and 30 mg/kg of nimodipine was administrated in positive control group, respectively filling the stomach for one time every day in each group, and continuously feeding the medicines for 7 days.

Jump-table training. The voltage of XT-911 type mouse jumping conditioned reflex tester was controlled to be 36V, and the test of the mouse learning-memory function was carried out after the last drug delivery was carried out in one hour. 10 minutes before training and 3 mg/kg of scopolamine hydrobromide were respectively injected into the model group and the dosing group respectively, and the blank control group was used for intraperitoneal injection of isovolumetric normal saline. Five mice were respectively delivered every batch and were operated in parallel, then injecting the second batch of mice after 10 minutes, and so on. During training, five mice in each batch were respectively placed into five grids of the jumping instrument, firstly adaptive to the environment for 3 minutes, then electrification was conducted, after the mouse was shocked, a plurality of mice jump platforms for avoiding electric shock. When the mouse was tripped, the double feet of the mouse contact the copper grid at the same time was deemed as electrically shocked, which was regarded as an error reaction, and they was trained for 5 minutes. The test was carried out again after 24 hours.

During testing, the mouse were placed on the jumping table, and time was counted at the same time. The first jumping time of the mouse was recorded, and it was an electric shock incubation period (namely, an error incubation period) and recording the times of jumping within 5 minutes (i.e., the times of errors), was recorded as observation index.

2.2 Influence on Sodium Nitrite-Induced Memory Consolidation Disorder of Mice

The grouping, administration and training methods were the same as the Experiment 2.1. After the training is finished, equal amount of normal saline was injected in blank control group, and the other groups were immediately subcutaneous injected with 90 mg/kg of sodium nitrite. The test was carried out after 24 hours. The test method is the same as that of the Experiment 2.1.

2.3 Influence on 40% Ethanol-Induced Memory Reproduction Disorder of Mice

The grouping, administration and training methods were the same as the Experiment 2.1. 30 minutes before test, the model group and the drug delivery group were gavage administrated with 10 ml/kg of 40% ethyl alcohol, the blank control group was provided with equal-volume distilled water. The test method was also same as the experiment 2.1.

3. Experimental Results 3.1 Influence of the Walnut Oligopeptide on the Scopolamine-Induced Memory Acquisition Impairment of the Mice The mice of scopolamine-induced memory acquisition impairment were administrated with the product of preparation example 1 (30, 100, 300 mg/kg) continuously for 7 d. In mice jumping table memory score, the medium-dose group and high-dose group of preparation example 1 can significantly prolong the incubation period, and the number of error was reduced. The result is shown in Table 11.

TABLE 11

Influence of the Walnut Oligopeptide on the Scopolamine-Induced Memory Acquisition Impairment of the Mice (n = 10)

| Group | Dose (mg/kg) | Incubation Period (s) | Times of Error (n) |
| --- | --- | --- | --- |
| Blank Group | / | 238.7 ± 105.2 | 1.1 ± 2.1 |
| Blank + Preparation Example 1 | 300 | 240.0 ± 111.5 | 0.4 ± 0.6 |

TABLE 11-continued

Influence of the Walnut Oligopeptide on the Scopolamine-Induced Memory Acquisition Impairment of the Mice (n = 10)

| Group | Dose (mg/kg) | Incubation Period (s) | Times of Error (n) |
|---|---|---|---|
| Model Group | / | 14.6 ± 11.0## | 3.5 ± 3.2# |
| Nimodipine Group | 30 | 35.9 ± 30.3 | 2.0 ± 1.4 |
| Preparation Example 1 | 30 | 21.5 ± 16.3 | 3.0 ± 1.4 |
| Preparation Example 1 | 100 | 184.6 ± 119.8** | 2.0 ± 2.0 |
| Preparation Example 1 | 300 | 226.5 ± 83.1** | 0.9 ± 0.8* |

$p < 0.05$,
$p < 0.01$, compared with blank group;
*$p < 0.05$,
**$p < 0.01$ compared with model group 3.2 Influence of Walnut Oligopeptide on Sodium Nitrite-Induced Memory Consolidation Disorder of Mice The mice of sodium nitrite-induced memory consolidation disorder were administrated with the product of preparation example 1 (30, 100, 300 mg/kg) continuously for 7 d. In mice jumping table memory score, every dose-group of Preparation Example 1 can significantly prolong the incubation period, and the number of error is reduced. The result is shown in Table 12.

TABLE 12

Influence of Walnut Oligopeptide on Sodium Nitrite-Induced Memory Consolidation Disorder of Mice (n = 10)

| Group | Dose (mg/kg) | Incubation Period (s) | Times of Error (n) |
|---|---|---|---|
| Blank Group | / | 221.2 ± 70.6 | 1.0 ± 0.95 |
| Blank + Preparation Example 1 | 300 | 218.3 ± 76.8 | 1.2 ± 1.2 |
| Model Group | / | 94.7 ± 49.3## | 3.6 ± 2.5## |
| Nimodipine Group | 30 | 237.7 ± 79.7** | 1.0 ± 1.2** |
| Preparation Example 1 | 30 | 252.8 ± 72.7** | 0.4 ± 0.6** |
| Preparation Example 1 | 100 | 273.2 ± 43.7** | 0.7 ± 1.5** |
| Preparation Example 1 | 300 | 240.7 ± 66.8** | 0.8 ± 1.0** |

$p < 0.01$, compared with blank group;
**$p < 0.01$, compared with model group 3.3 Influence of Walnut Oligopeptide on 40% Ethanol-Induced Memory Reproduction Disorder of Mice The mice of memory reproduction disorder were administrated with the product of Preparation Example 1 (30, 100, 300 mg/kg) continuously for 7 d. In mice jumping table memory score, every dose-group of preparation example 1 can significantly prolong the incubation period, and the number of error was reduced. The result is shown in Table 13.

TABLE 13

Influence of Walnut Oligopeptide on 40% Ethanol-Induced Memory Reproduction Disorder of Mice (n = 8)

| Group | Dose (mg/kg) | Incubation Period (s) | Times of Error (n) |
|---|---|---|---|
| Blank Group | / | 212.0 ± 84.2 | 0.8 ± 0.9 |
| Blank + Preparation Example 1 | 300 | 164.3 ± 97.01 | 2.2 ± 2.1 |
| Model Group | / | 46.3 ± 26.5## | 5.7 ± 2.9## |
| Nimodipine Group | 30 | 99.6 ± 98.7 | 2.5 ± 1.4* |
| Preparation Example 1 | 30 | 199.3 ± 75.5** | 2.0 ± 2.0** |

TABLE 13-continued

Influence of Walnut Oligopeptide on 40% Ethanol-Induced Memory Reproduction Disorder of Mice (n = 8)

| Group | Dose (mg/kg) | Incubation Period (s) | Times of Error (n) |
|---|---|---|---|
| Preparation Example 1 | 100 | 142.1 ± 113.5** | 2.8 ± 2.2* |
| Preparation Example 1 | 300 | 146.1 ± 73.8** | 3.2 ± 3.4 |

$p < 0.01$, compared with blank group;
*$p < 0.05$,
**$p < 0.01$, compared with model group The learning-memory function comprises space learning memory function and non-spatial learning memory function. The memory disorder model is an effective means for evaluating the influence of the medicine on the memory process, and also serves as a model that is commonly used for studying the senile dementia and the action mechanism thereof. Scopolamine is a M-receptor blocker, which may block agonistic action of acetylcholine to M-receptors and stimulating the learning-memory dysfunction caused by insufficient acetylcholine. Sodium nitrite can denature hemoglobin, and causing ischemia and anoxia of the brain tissue, and damaging learning-memory processes. Ethanol may inhibit the neuro-functional activity of cerebral cortex and the conditioned reflex process of the animal, hindering the synthesis of protein and RNA in the brain. Choline may bring some changes to the dopamine system, thereby destroying learning-memory function and causing learning-memory reproduction disorder. In the model and the dosage range selected by the experiment, the medium-dose and high-dose group of walnut oligopeptide can improve incubation period of mice of scopolamine-induced learning-memory acquisition impairment to different degree. For high-dose group, the number of error of jumping from platform can be reduced. For sodium nitrite-induced memory consolidation disorder model, every dose group of walnut oligopeptide can prolong the incubation period, and the number of error can be reduced. In 40% ethanol-induced memory acquisition impairment of mice experiment, every dose group of walnut oligopeptide can significantly prolong the incubation period, and the number of error can be reduced. Therefore, the medium-dose and high-dose group of walnut oligopeptide can have an obvious improvement effect on scopolamine-induced learning-memory ability of mice with learning-memory acquisition impairment. And the low-dose, medium-dose and high-dose group can have a significant improvement effect on 40% ethyl alcohol-induced learning-memory reproduction disorder model of mice and sodium nitrite-induced learning-memory consolidation disorder model of mice.

What is claimed is:
1. A composition, comprising:
a walnut oligopeptide powder, having a peptide content of more than 80 wt %, wherein more than 95% of the walnut oligopeptide has a molecular weight of less than 1500 Dalton, and a molecular weight distribution of the walnut peptide is as follows:

| Molecular Weight Dalton Distribution | |
|---|---|
| Range of Molecular Weight | Peak Area Percentage %, λ 220 nm |
| >1500 | <1 |
| 1500~1300 | 7~8 |

-continued

| Molecular Weight Dalton Distribution | |
|---|---|
| Range of Molecular Weight | Peak Area Percentage %, λ 220 nm |
| 1300~500 | 20~25 |
| 500~200 | 50~55 |
| <200 | <20 |

Range of number-average molar mass: 170~3000
Range of Weight-Average Molar Mass: 180~4000;

and
   an acceptable additive in medicine, food, health-supplement or cosmetics,
   wherein the composition has a dosage form selected from the group consisting of film-coated tablet, sugar-coated tablet, enteric-coated tablet, dispersible tablet, capsules.

\* \* \* \* \*